United States Patent [19]

Letton et al.

[11] Patent Number: 5,646,319

[45] Date of Patent: Jul. 8, 1997

[54] SYNTHESIS OF N-ACYL-N-ALKYLCARBOXYLATES

[75] Inventors: James Carey Letton, Forest Park; Larry Eugene Miller, Cincinnati, both of Ohio

[73] Assignee: The Procter & Gamble Company, Cincinnati, Ohio

[21] Appl. No.: 493,976

[22] Filed: Jun. 23, 1995

[51] Int. Cl.$^6$ ................................................ C07C 231/00
[52] U.S. Cl. ........................... 554/69; 554/68; 554/132; 554/163
[58] Field of Search ....................... 584/163, 132, 584/68, 69

[56] References Cited

U.S. PATENT DOCUMENTS

| | | | |
|---|---|---|---|
| 2,384,817 | 9/1945 | Chitwood | 260/531 |
| 2,804,474 | 8/1957 | Lew | 260/534 |
| 2,956,068 | 10/1960 | Dohr et al. | 260/404.5 |
| 3,457,302 | 7/1969 | Boardman | 260/534 |
| 3,475,489 | 10/1969 | de Graaf et al. | 260/534 |
| 3,763,234 | 10/1973 | Brill | 260/558 |
| 3,864,369 | 2/1975 | Isa et al. | 260/413 |
| 3,910,973 | 10/1975 | Isa et al. | 260/413 |
| 3,957,838 | 5/1976 | Nishino et al. | 260/410.9 R |
| 3,997,578 | 12/1976 | Sheng | 260/413 |
| 4,801,742 | 1/1989 | Quirk et al. | 562/450 |

*Primary Examiner*—Deborah D. Carr
*Attorney, Agent, or Firm*—Thomas G. Krivulka

[57] ABSTRACT

Chemical synthesis of N-acyl-N-alkylcarboxylates through oxidation of substituted amides formed from carboxylic acid esters and an N-alkyl-N-alkanolamine.

20 Claims, No Drawings

SYNTHESIS OF N-ACYL-N-ALKYLCARBOXYLATES

FIELD OF THE INVENTION

The present invention relates to the chemical synthesis of N-acyl-N-alkylcarboxylate compounds.

BACKGROUND OF THE INVENTION

The use of N-acyl-N-alkylcarboxylates as surfactants is well known. The combination of amido and carboxylate functional groups, coupled with the ability to incorporate a broad range of alkyl substituents, provides a highly desirable range of surfactant properties. Of this class of compounds, the sarcosinates have the widest commercial application. Unfortunately, the synthesis of N-acyl-N-alkylcarboxylates in general, and of sarcosinates in specific, presents a relatively costly approach to address the needs of the surfactant community.

N-acyl-N-alkylcarboxylates have historically been synthesized by reacting the sodium salt of an N-substituted amino acid with a fatty acid chloride in the presence of a strong base. The common industrial method of producing these fatty acid chlorides includes the use of phosphorus trichloride. Fatty acid chlorides produced this way tend to retain trace levels of inorganic or organic phosphorus compounds. These trace impurities often are retained through subsequent steps and lead to undesirable murkiness or cloudiness in the final product.

To further complicate matters, N-substituted amino acids are not common naturally occurring amino acids, and must themselves be produced using rather severe conditions. For example, sarcosine, also known as methyl glycine, is produced by reacting hydrogen cyanide with formaldehyde to form a glycolic nitrile. This nitrile is then condensed with methylamine forming methylaminonitrile. The methylaminonitrile is then hydrolyzed with strong alkali to the sarcosine salt. These relatively costly and undesirable syntheses lessen the commercial attractiveness of sarcosinates for broad use.

The object of the present invention is to provide an alternative route to the commercially valuable N-acyl-N-alkylcarboxylate class of compounds. The invention's reaction sequences eliminate the use of N-substituted amino acids and acid chlorides. Hazardous chemicals typically employed in, for example, the synthesis of sarcosine, such as formaldehyde, hydrogen cyanide, and all nitrile intermediates, are thus avoided. Removing acid chlorides from the synthetic scheme also has the benefit of removing a source of troublesome inorganic and organic phosphorous impurities from the final product. The present invention provides a direct, cost effective alternative to N-acyl-N-alkylcarboxylate synthesis.

BACKGROUND ART

The following references are instructive: U.S. Pat. No. 2,720,540, issued Oct. 11, 1955, for synthesis of sarcosine; Japanese Sho 61-216724, laid open Sep. 26, 1987, for synthesis of sarcosinates from sarcosine with acid chlorides; U.S. Pat. Nos. 3,836,551, issued Sep. 17, 1974, and 4,380,646, issued Apr. 19, 1983, for synthesis of N-acylamino carboxylic acids from amino acids reacted with carboxylic acids, esters and amides; and Jerry March, *Advanced Organic Chemistry* 9–22 (3rd ed. 1985), for general discussion of oxidation of alcohols to acids.

SUMMARY OF THE INVENTION

This development relates to a method for preparing N-acyl-N-alkylcarboxylates, and salts thereof, of the formula;

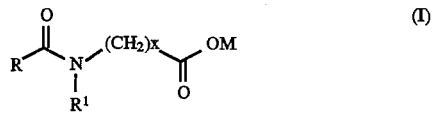

wherein R is a $C_1$ or higher hydrocarbyl substituent, $R^1$ is a $C_1$–$C_6$ hydrocarbyl substituent, x is an integer from 1 to 6, and M is a cationic moiety, preferably selected from alkali metal salts and hydrogen, comprising the steps of;

(a) reacting, in the presence of a base catalyst, a N-alkyl-N-alkanolamine of the formula

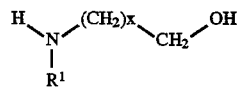

wherein $R^1$ and x are as described before; with a carboxylic acid ester of the formula

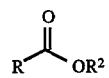

wherein R is as described before, $R^2$ is a $C_1$ or higher hydrocarbyl substituent, to form, after work up, a N-alkyl-N-hydroxyalkylamide of the formula;

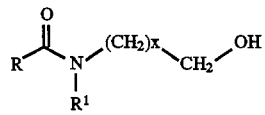

and;

(b) oxidizing the hydroxy group on said amide to a carboxy group; and (c) optionally, neutralizing the N-acyl-N-alkylcarboxylate formed by step (b) to form the N-acyl-N-alkylcarboxylate salt (I), whereby M is an alkali metal cation.

The preferred method for preparing the amidation product of step (a) is conducted at a temperature from about 80° C. to about 200° C., and preferably at the reflux temperature of the solution. Most preferably reduced pressure is employed, sufficient to maintain the reflux temperature at from about 95° C. to about 105° C.

The carboxylic ester employed in said step (a) has a hydrocarbyl R group of $C_1$ to $C_{24}$, preferably $C_8$ to $C_{18}$, and most preferably $C_{12}$ to $C_{18}$. The $R^2$ substituent may be methyl or ethyl, and most preferably is methyl.

The process of step (a) can proceed with or without an added solvent. Solvents, preferably with boiling points above about 65° C. and below about 200° C., can be used to facilitate mixing of the reactants. Most preferably excess N-alkyl-N-alkanolamine can function as a solvent and can be recovered for reuse by distillation after the reaction. In order to minimize reaction time, it is preferable to use a basic catalyst such as sodium or potassium alkoxide.

The step (a) reaction normally provides a yield of about 85%–90% of theory based on the amount of ester used with a molar ratio of N-alkyl-N-alkanolamine reactant to ester reactant of from about 20:1 to about 1:1 and a molar ratio of ester reactant to basic catalyst of from about 0.05:1 to about 0.2 to 1.

The amide product of step (a) is then used as a reactant for the oxidation step (b). A variety of well known oxidation methods can be employed to convert the alcohol functionality to a carboxylic acid group, including, but not limited to, the use of $Na_2Cr_2O_7$ in aqueous $H_2SO_4$ or aqueous acetic acid, $CrO_3/H_2SO_4$ (Jone's Reagent), pyridinium dichromate, and where the amide is free of any unsaturated alkyl substituents, $CrO_3$ in pyridine, permanganates, nitric acid, and oxygen with catalyst. Said reaction is carried out in a solvent inert to the oxidation conditions of step (b), and preferably having a boiling point below about 100° C. in order to facilitate work up of the reaction mixture. Preferably, the oxidation is performed with Jone's Reagent, and most preferably using a mixture of dichloromethane and acetone as a solvent. The preferred method of preparing the oxidation product of step (b) is conducted at a temperature from about 30° C. to about 60° C., and most preferably from about 35° C. to about 50° C.

The step (b) reaction normally provides a yield of from about 85% to about 95% of theory based on the amount of said amide used.

The sarcosinate amido acid product of step (b) can optionally be converted to the sarcosinate amido acid salt by neutralization with an alkali metal base.

All percentages, ratios and proportions herein are on a mole basis, unless otherwise specified. All references are incorporated by reference.

DETAILED DESCRIPTION OF INVENTION

The reaction sequence for the synthesis of a specific N-acyl sarcosinate is shown below. The reaction sequence, as illustrated, employs methyl laurate, sodium methoxide, and chromic/sulfuric acid, but this is only by way of illustration and not limitation, as will be seen hereinafter.

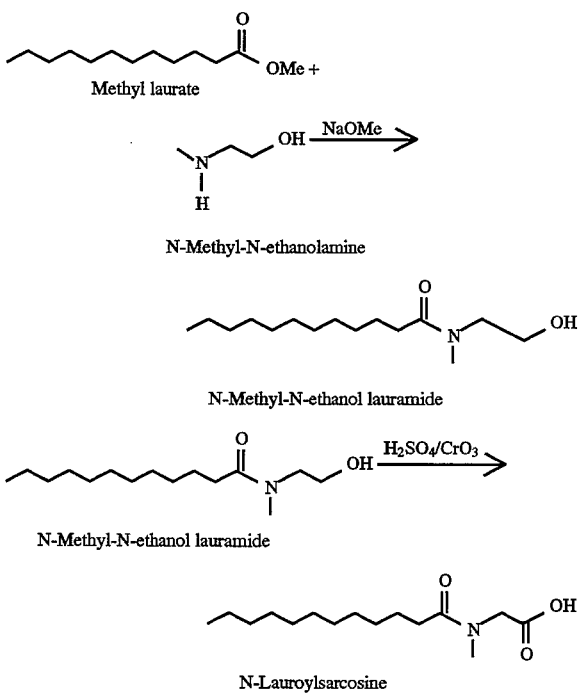

The following is by way of illustration, and not limitation, of reactants, conditions, equipment and the like, useful in the instant process.

Amidation Reaction Process: The carboxylic acid ester reactant can be selected from alkyl esters (preferably methyl or ethyl) of straight chain aliphatic, saturated or unsaturated, branched chain aliphatic, ethercarboxylic and cycloaliphatic carboxylic acids. Nonlimiting examples include methyl or ethyl esters of the following carboxylic acids: acetic, propionic, butyric, caprylic, caproic, nonanoic, decanoic, lauric, myristic, palmitic, stearic, oleic, linoleic, behenic, 2-methyl-undecanoic, 2-butyl-octanoic, 2-ethyl-hexanoic, 3,5,5-trimethylhexanoic, and mixtures thereof. Methyl ester mixtures derived from natural oils such as cocoyl, tallowyl, and mixtures thereof are preferred. Methyl ester mixtures derived from high oleic content natural oils (preferably having at least about 60%, more preferably at least about 75%, and most preferably at least about 90% oleic content) are especially preferred.

A solvent can be added to facilitate mixing and dissolution of the reactants. It is preferred that the solvent boiling point be less than 200° C., if it must be removed from the reaction product. It is further preferred that the solvent have a boiling point greater than about 65° C. in order to allow sufficient reflux temperature for reaction to occur. Solvents such as, but not limited to, toluene, heptane, tetrahydrofuran, cyclohexane are suitable. Excess N-alkyl-N-alkanolamine is the preferred solvent, since the excess will increase the reaction rate and can later be removed by distillation for reuse.

A base with a pKa equal to, or greater than, alkoxides is necessary to catalyze amidation. Various alkoxides are suitable such as sodium methoxide, potassium methoxide, sodium ethoxide, and potassium ethoxide. Bases capable of forming alkoxides from alcohols are also suitable including sodium metal, potassium metal, sodium hydride and potassium hydride. Sodium methoxide is the preferred base.

The reaction can be carried out under vacuum, or atmospheric reflux conditions. Reaction temperatures will typically be above about 65° C. and below about 200° C. Where reflux temperatures above about 120° C. are employed, the introduction of an inert gas such as argon, nitrogen or helium is useful to remove traces of atmospheric oxygen that may lead to darkening of the reaction mixture. Preferably, vacuum conditions are employed so as to lower the reflux temperature of the reaction mixture. Most preferably, vacuum conditions are employed so as to lower the reflux temperature of the reaction mixture to the range of from about 95° C. to about 105° C. and to remove the alcohol generated as the reaction proceeds. Reaction times can vary, of course, depending upon the ratio of reactants being employed. However, as a general rule, a reaction time from about 4 to about 16 hours is sufficient.

Reaction stoichiometry in the amidation step employs a molar ratio of N-alky-N-alkanolamine reactant to ester reactant of from about 20:1 to about 1:1 and a molar ratio of ester reactant to basic catalyst of from about 0.05:1 to about 0.2 to 1.

The reaction is complete upon the consumption of carboxylic acid ester reactant as determined by an analytical technique such as thin layer chromatography. Any excess N-alkyl-N-alkanolamine and solvent can then be removed from the mixture by either atmospheric or vacuum distillation and recycled for use in later synthesis. The product can be obtained in purified form by conventional work up methods such as dissolving the resulting amidation liquors in an organic solvent and washing with water to remove the basic catalyst. These organic liquors can be concentrated under vacuum to yield the amidation product typically in about 90% to 95% yield.

Oxidation Reaction Process: The amidation product is treated under oxidation conditions sufficient to convert the hydroxy functionality of the substituted amide to a carboxylic acid. Oxidation methods including, but not limited to, the use of $Na_2Cr_2O_7$ in aqueous $H_2SO_4$ or aqueous acetic acid, $CrO_3/H_2SO_4$ (Jone's Reagent), pyridinium dichromate, and where the amide R group is free of any unsaturated alkyl substituents, $CrO_3$ in pyridine, $KMnO_4$, $Zn(MnO_4)_2$, nitric acid, and oxygen with catalyst. Preferably, Jone's reagent is used to perform the oxidation.

The reaction conditions for a Jone's reagent oxidation can be as follows. The amidation product is stirred at room temperature in a solvent inert to the Jone's reagent oxidation conditions. It is preferable that the solvent have a boiling point below about 100° C. to facilitate removal by distillation after the reaction. Suitable solvents include, but are not limited to, acetone, dichloromethane, tetrahydrofuran, ethyl ether, and combinations thereof. A mixture of acetone and dichloromethane at about a 5:1 ratio is preferred.

The reaction mixture is generally warmed to about 35° C. to about 50° C. at which point the Jone's reagent is added. Typically, the Jone's reagent is used in excess, with a molar ratio of Jone's reagent to amidation product generally in the range of from about 2:1 to about 6:1. Preferably, the molar ratio of Jone's reagent to amidation product is in the range of from about 3:1 to about 5:1. The reaction is typically rapid and generally complete in about 30 minutes to one hour.

The reaction product can be worked up under conventional conditions. During the Jone's reagent oxidation, chromium salts form that can cause gums in the reaction vessel. These salts can be dissolved by the addition of water during the work up of the reaction. The addition of water forms two phases which exist as an aqueous layer and an organic layer. The aqueous layer can be drained and the organic layer washed repeatedly with additional water to remove undesired salts. The organic layer can then be dried and concentrated to yield the final product in yields typically ranging from about 85% to about 95% of theory based upon the amount of amidation product used.

Optionally, the resulting N-acyl-N-alkylcarboxylate can be converted to an alkali metal salt form by neutralization with an alkali metal base such as sodium or potassium hydroxide.

EXAMPLE I

A. Synthesis of N-methyl-N-ethanol stearamide—A 250 mL, 2-neck round bottom flask is fitted with thermometer, reflux condenser, magnetic stirrer, and a water aspirator vacuum source. The reaction vessel is charged with methyl stearate (15.0 g, 0.05 mol), N-methyl-N-ethanolamine (37.8 g, 0.50 mol), and potassium methoxide (0.7 g, 0.01 mol). The reaction is placed under aspirator vacuum and heated to 105° C. while stirring. The reaction is kept at 105° C. under aspirator vacuum for 8 hr. The excess N-methyl, N-ethanolamine and residual methanol is then distilled off under vacuum. The reaction is cooled, dissolved in 200 mL dichloromethane, and washed with water two times. The dichloromethane layer is concentrated under vacuum and the desired product (14.5 g) is obtained.

B. Synthesis of stearoyl sarcosine—A 1 L, 3-neck round bottom flask is fitted with thermometer, reflux condenser, and mechanical stirrer. The reaction vessel is charged with acetone (250 mL), dichloromethane (50 mL), and N-methyl, N-ethanol stearamide (5 g, 0.015 mol). The reaction mixture is stirred and heated to 38° C. Jone's reagent (8 mL, 8N solution) is added in one portion with stirring. The reaction is allowed to stir for one hour at ambient temperature. Water (100 mL) is then added and the solution diluted with dichloromethane (100 mL). The reaction mixture is transferred to a 1 L separatory funnel and the organic layer washed three times with water (100 mL each), dried, and concentrated under vacuum to obtain the desired product (4.9 g).

EXAMPLE II

A. Synthesis of N-methyl, N-hydroxyethyltallow amide—(NOTE-the tallow derived methyl ester of this example is composed of 70% octodecanoic and 30% hexadecanoic, hydrogenated methyl ester, the ester composition having an average molecular weight of 289.5 g/mol)

A 250 mL reaction flask is fitted with thermometer, reflux condenser, overhead stirrer, heating mantle and a vacuum source past the condenser. The reaction flask is charged with tallow methyl ester (20 g, 0.069 mol), N-methyl, N-ethanolamine (51.81 g, 0.69 mol), and potassium methoxide (0.8 g, 0.014 mol). The reaction is placed under vacuum and heated to 105° C. while stirring. Methanol is removed from the reaction as it forms. The reaction was run for eight hours while stirring at 105° C. The reaction is then set up for vacuum distillation to remove the excess N-methyl, N-ethanolamine and any residual methanol.

The reaction is then allowed to cool back to room temperature, then dissolved in dichloromethane. The solution is washed several times with water, then separated and dried over $Na_2SO_4$. After standing overnight, the solution is filtered to remove the $Na_2SO_4$ and stripped to dryness yielding 21.5 g of the desired product.

B. Synthesis of tallowyl sarcosine—A 1 L, 3-neck round bottom flask is fitted with thermometer, reflux condenser, dropping funnel, and mechanical stirrer. The reaction vessel is charged with N-methyl, N-hydroxyethyltallow amide (20.0 g, 0.06 mol, as prepared in Step II A. above), 300 ml acetone and 50 ml dichloromethane. The mixture is stirred and warmed to 35° C. The chromic acid solution (Jone's Reagent, 30 ml of 8N solution) is placed in the dropping funnel and added slowly to the reaction mixture while the temperature is maintained below 40° C. After addition is complete and blue chromium salts have precipitated, the reactor is stirred at room temperature for one hour. After one hour, the solution shows a slight orange color from excess chromic acid. Isopropyl alcohol is added dropwise until the orange color is dispersed. The reaction mixture is diluted with water and 200 mL of dichloromethane. The mixture is transferred to a separatory funnel, and the organic layer washed several times with water. The washed organic layer is dried over anhydrous $Na_2SO_4$, filtered through a celite bed and stripped under vacuum to yield 19.5 g of the desired product. The product is verified by I.R. spectroscopy.

EXAMPLE III

A. Synthesis of N-methyl, N-hydroxyethyloleyl amide—A 250 mL reaction flask is fitted with thermometer, reflux condenser, overhead stirrer, heating mantle and a vacuum source past the condenser. The reaction flask is charged with oleyl methyl ester (20.7 g, 0.07 mol), N-methyl, N-ethanolamine (52.5 g, 0.7 mol), and potassium methoxide (0.8 g, 0.014 mol). The reaction is placed under vacuum and heated to 100° C. while stirring. The reaction was run for seven hours while stirring at 100° to 105° C. The reaction is then set up for vacuum distillation to remove the excess N-methyl, N-ethanolamine and any residual methanol.

The reaction is then allowed to cool back to room temperature, then dissolved in 250 mL dichloromethane. The solution is washed several times with water. The organic layer is then separated and dried over $Na_2SO_4$. After standing overnight, the solution is filtered to remove the $Na_2SO_4$ and stripped to dryness yielding 23.0 g of the desired product. The product is verified by I.R. spectroscopy.

B. Synthesis of oleyl sarcosine—A 1 L, 3-neck round bottom flask is fitted with thermometer, reflux condenser, dropping funnel, and mechanical stirrer. The reaction vessel is charged with N-methyl, N-hydroxyethyltallow amide (20.0 g, 0.0589 mol, as prepared in Step III. A above), 300 ml acetone and 50 ml dichloromethane. The mixture is stirred and warmed to 35° C. The chromic acid solution (Jone's Reagent, 29.4 ml of 8N solution) is placed in the dropping funnel and added slowly to the reaction temperature is maintained below 40° C. After addition is complete and blue chromium salts have precipitated, the reactor is stirred at room temperature for 45 minutes. A few drops of isopropyl alcohol is then added to remove excess chromic acid. The reaction mixture is diluted with water and 200 mL of dichloromethane. The mixture is transferred to a separatory funnel, and the organic layer washed several times with brine. The washed organic layer is dried over anhydrous $Na_2SO_4$, filtered through a celite bed and stripped under vacuum to yield 19 g of the desired product. The product is verified by I.R. spectroscopy.

What is claimed is:

1. A method for preparing N-acyl-N-alkylcarboxylates and salts thereof of the formula

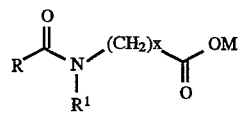

wherein R is a $C_1$ or higher hydrocarbyl substituent, $R^1$ is a $C_1$–$C_6$ $C_6$ hydrocarbyl substituent, x is an integer from 1 to 6, and M is a cationic moiety selected from alkali metal salts and hydrogen, comprising the steps of;

(a) reacting, in the presence of a base catalyst, a N-alkyl-N-alkanolamine of the formula

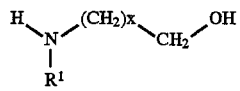

wherein $R^1$ and x are as described before; with a carboxylic acid ester of the formula

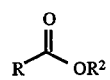

wherein R is as described before, $R^2$ is a $C_1$ or higher hydrocarbyl substituent, to form, after work up, a N-alkyl-N-hydroxyalkylamide of the formula;

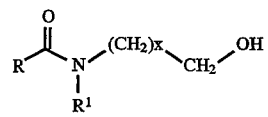

and;

(b) oxidizing the hydroxy group on said amide to a carboxy group; and (c) optionally, neutralizing the N-acyl-N-alkylcarboxylate formed by step (b) to form the N-acyl-N-alkylcarboxylate salt (I), whereby M is an alkali metal cation.

2. The method according to claim 1 wherein R is $C_6$ to $C_{24}$ and $R^2$ is methyl or ethyl.

3. The method according to claim 1 wherein the reaction step (a) is catalyzed by alkoxide base.

4. The method according to claim 3 wherein the alkoxide base is selected from the group consisting of sodium methoxide, potassium methoxide, sodium ethoxide, potassium ethoxide, sodium t-butoxide, potassium t-butoxide, and mixtures thereof.

5. The method according to claim 1 wherein the N-alkyl-N-alkanolamine in reaction step (a) is N-methyl-N-ethanolamine.

6. The method according to claim 5 wherein the reaction step (a) utilizes a solvent selected from the group consisting of excess N-alkyl-N-alkanolamines, toluene, heptane, tetrahydrofuran, cyclohexane.

7. The method according to claim 6 wherein the reaction step (a) utilizes excess N-methyl-N-ethanolamine as a solvent.

8. The method according to claim 1 wherein the reaction step (a) utilizes a molar ratio of N-alkyl-N-alkanolamine to carboxylic acid ester of greater than about 1 to less than about 20.

9. The method according to claim 1 wherein the carboxylic acid ester is selected from the group consisting of cocoyl and tallowyl derived esters and mixtures thereof.

10. The method according to claim 1 wherein the carboxylic acid ester contains at least 60% oleic acid ester.

11. The method according to claim 1 wherein the reaction step (b) utilizes an oxidation method selected from the group consisting of methods using $Na_2Cr_2O_7$ in aqueous $H_2SO_4$, $Na_2Cr_2O_7$ in aqueous acetic acid, $CrO_3/H_2SO_4$ (Jone's Reagent), pyridinium dichromate, $KMnO_4$, $Zn(MnO_4)_2$, nitric acid, and oxygen with catalyst.

12. The method according to claim 11 wherein the oxidation method in step (b) uses $CrO_3/H_2SO_4$ (Jone's Reagent).

13. The method according to claim 12 wherein the reaction step (b) utilizes a solvent with a boiling point below about 100° C.

14. The method according to claim 13 wherein the reaction step (b) utilizes a solvent selected from the group consisting of acetone, dichloromethane, tetrahydrofuran, ethyl ether, and mixtures thereof.

15. A method for preparing hydrogenated tallowyl sarcosinate amido acids and salts thereof, comprising the steps of;

(a) reacting, in the presence of an alkoxide base catalyst N-methyl-N-ethanolamine with a hydrogenated tallowyl ester to form, after work up, a N-methyl, N-hydroxyethylamide; and (b) oxidizing the hydroxy group on said amide to a carboxy group; and (c) optionally, neutralizing the sarcosinate amido acid formed by step (b) to form the sarcosinate amido acid salt.

16. The method according to claim 15 wherein the hydrogenated tallowyl ester is selected from methyl ester, ethyl ester, and mixtures thereof, and the alkoxide base catalyst in step (a) is selected from the group consisting of sodium methoxide, sodium ethoxide, sodium t-butoxide, potassium methoxide, potassium ethoxide, potassium t-butoxide, and mixtures thereof.

17. The method according to claim 16 wherein the reaction step (a) utilizes a solvent selected from the group consisting of excess N-methyl-N-ethanolamine, toluene, heptane, tetrahydrofuran, cyclohexane.

18. The method according to claim 17 wherein the reaction step (a) utilizes a molar ratio of N-methyl-N- ethanolamine to carboxylic acid ester of greater than about 1 to less than about 20.

19. The method according to claim 18 wherein the reaction step (b) utilizes an oxidation method selected from the group consisting of $Na_2Cr_2O_7$ in aqueous $H_2SO_4$, $Na_2Cr_2O_7$ in aqueous acetic acid, $CrO_3/H_2SO_4$ (Jone's Reagent), pyridinium dichromate, $KMnO_4$, $Zn(MnO_4)_2$, nitric acid, and oxygen with catalyst.

20. A method for preparing oleyl sarcosinate amido acids and salts thereof, comprising the steps of;

(a) reacting, in the presence of sodium methoxide catalyst N-methyl-N-ethanolamine with an oleyl methyl ester to form, after workup, a N-methyl-N-hydroxyethylamide; and (b) oxidizing the hydroxy group on said amide to a carboxy group using $CrO_3/H_2SO_4$ (Jone's Reagent); and (c) optionally, neutralizing the sarcosinate amido acid formed by step (b) to form the sarcosinate amido acid salt.

* * * * *